United States Patent [19]

Nakatomi et al.

[11] 3,943,186

[45] Mar. 9, 1976

[54] METHOD FOR PRODUCING ISOPENTENE

[75] Inventors: Shunsuke Nakatomi, Chiba; Takemi Yamamura, Ichihara; Yoshikazu Akiba, Chiba, all of Japan

[73] Assignee: Ube Industries, Ltd., Ube, Japan

[22] Filed: Dec. 13, 1974

[21] Appl. No.: 532,451

[30] Foreign Application Priority Data

Dec. 28, 1973  Japan.............................. 48-144682

[52] U.S. Cl...... 260/683 D; 252/463; 260/683.15 R
[51] Int. Cl.²........................................... C07C 3/62
[58] Field of Search................ 260/683 D, 683.15 R

[56] References Cited
UNITED STATES PATENTS

| | | | |
|---|---|---|---|
| 2,288,872 | 7/1942 | Anderson et al. | 260/683.15 |
| 3,595,920 | 7/1971 | Ellis et al. | 260/683 |
| 3,637,891 | 1/1972 | McGrath et al. | 260/683 |
| 3,786,112 | 1/1974 | Reusser et al. | 260/683 |
| 3,872,180 | 3/1975 | Nakatomi et al. | 260/683 |

*Primary Examiner*—Delbert E. Gantz
*Assistant Examiner*—C. E. Spresser

[57] ABSTRACT

Isopentene is produced in a high yield by a method wherein disproportionation of a hydrocarbon mixture containing n-butene and isobutene is carried out by bringing, at 200 to 350 C, the hydrocarbon mixture into contact with a composite catalyst which has been prepared by depositing a barium or strontium compound and a silver compound onto a carrier material consisting of an activated high purity alumina carrier to produce a precursory composite catalyst, calcining the precursory composite catalyst at 300 to 900 C, and isolating the resulted isopentene from the reaction mixture.

21 Claims, No Drawings

METHOD FOR PRODUCING ISOPENTENE

The present invention relates to a method for producing isopentene, more particularly, relates to a method for producing isopentene by disproportionation of isobutene and n-butene contained in a hydrocarbon mixture.

The term "isopentene" used herein refers to 2-methylbutene-1, 2-methylbutene-2, 3-methylbutene-1 or mixtures of two or more of the above-mentioned compounds.

The term "n-butene" used herein refers to cis-butene-2, trans-butene-2, butene-1 or mixtures of two or more of the above-mentioned butenes.

It is known that olefins, for example, a hydrocarbon mixture containing isobutene or n-butene, may be disproportionated by bringing them into contact with a catalyst, for example, molybdenum oxide or rhenium oxide. However, it is also known that the conventional disproportionation method using the above-mentioned catalyst involves the disadvantages that $C_5$ fraction in the resultant disproportionation product contains a relatively small content of isopentene and a relatively large content of n-pentene and, therefore, that isolation and purification of the resultant isopentene are complicated. Accordingly, the conventional disproportionation method is not usable practically in industry.

The term "$C_5$ fraction" used herein refers to a fraction of distillate consisting essentially of hydrocarbons having five carbon atoms, separated from the disproportionation product.

An object of the present invention is to provide a method for producing a high yield of isopentene by disproportionation of a hydrocarbon mixture containing isobutene and n-butene such that the hydrocarbon mixture can be disproportionated in a high conversion. The $C_5$ fraction in the resultant disproportionation product contains a very high content of isopentene and the resultant isopentene is easily isolated and purified from the disproportionation mixture.

The above object can be accomplished by the method of the present invention which comprises the steps of:

providing a composite catalyst which has been prepared from 100 parts by weight of a carrier material consisting of an activated high purity alumina, 0.5 to 5 parts by weight of a barium or strontium compound calculated in terms of an oxide thereof and 1 to 20 parts by weight of a silver compound calculated in terms of silver metal by depositing said barium or strontium compound and said silver compound onto said alumina carrier to produce a precursory composite catalyst and calcining the precursory composite catalyst at a temperature of 300° to 900°C;

disproportionating a hydrocarbon mixture containing isobutene and n-butene by bringing it into contact with said composite catalyst at a temperature of 200° to 350°C, and;

isolating the resultant isopentene from the reaction mixture.

The disproportionation step in the method of the present invention may result in isomerization, dimerization and decomposition of a minor portion of the hydrocarbon mixture while the major portion of the hydrocarbon mixture is disproportionated. Accordingly, the term "disproportionation" used herein includes the isomerization, dimerization and decomposition of the minor portion of the hydrocarbon mixture in addition to the true disproportionation of the major portion of the hydrocarbon mixture.

According to the method of the present invention, the disproportionation product essentially consists of a hydrocarbon mixture of $C_5$ fraction containing 95% by weight or more of isopentene, propylene and $C_{+6}$ fraction. The term "$C_{+6}$ fraction" used herein refers to a fraction of distillate consisting essentially of hydrocarbons having 6 or more carbon atoms, separated from the disproportionation product. That is, the disproportionation product of the present invention consists essentially of a major portion of olefins and a very minor portion of saturated hydrocarbons. Also, it should be noted that the content of the $C_{+6}$ fraction in the disproportionation product is at most, 25% by weight and, therefore, the major portion of olefin in the disproportionation product consists of propylene and isopentene both of which are very valuable to the chemical industries.

Further, it is important that the method of the present invention can disproportionate the hydrocarbon mixture with a high degree of disproportionation conversion. The term "disproportionation conversion" used herein refers to the ratio in percent of the weight of the disproportionation product to the original weight of the hydrocarbon mixture subjected to the disproportionation process. The catalyst usable for the disproportionation step in the method of the present invention is a composite catalyst which has been prepared by depositing 0.5 to 5 parts by weight of a barium or strontium compound, calculated in terms of an oxide thereof, and 1 to 20 parts by weight of a silver compound, calculated in terms of silver metal, onto a carrier material consisting of an activated high purity alumina in an amount of 100 parts by weight to produce a precursory composite catalyst and calcining the precursory composite catalyst at a temperature of 300° to 900°C.

The barium compound usable for the method of the present invention may be selected from the group consisting of barium salts of inorganic acids, barium salts of organic acid having 1 to 6 carbon atoms, barium hydroxide and barium oxide. The barium salts of inorganic acid may be selected from barium nitrate, barium sulfate, barium carbonate, barium chloride, and mixtures of two or more of the above-mentioned compounds.

The barium salt of the organic acid may be selected from the group consisting of barium formate, barium acetate, barium propionate, barium n-butyrate, barium isobutyrate, barium n-valerate, barium isovalerate, barium n-caproate, barium pivalate, barium acrylate, barium methacrylate, barium crotonate, barium oxalate, barium malonate, barium succinate and mixture of two or more of the above-mentioned compounds.

The strontium compound usable as a component of the composite catalyst for the method of the present invention may be selected from the group consisting of strontium salts of inorganic acids, strontium salts of organic acids having 1 to 6 carbon atoms, strontium oxide, strontium hydroxide and mixtures of two or more of the above-mentioned compounds. THe strontium salt of inorganic acid may be selected from the group consisting of strontium nitrate, strontium sulfate, strontium carbonate, strontium chloride and mixtures of two or more of the above-mentioned compounds. The strontium salt of organic salt may be selected from the group consisting of strontium formate, strontium acetate, strontium propionate, strontium n-butyrate, strontium isobutyrate, strontium n-valerate, strontium isovalerate, strontium n-caproate, strontium pivalate, strontium acrylate, strontium methacrylate, strontium crotonate, strontium oxalate, strontium malonate, strontium succinate and mixtures of two or more of the above-mentioned compounds.

The silver compounds usable as a component of the composite catalyst for the method of the present invention may be selected from the group consisting of silver nitrate, silver sulfate, silver carbonate, silver halides, silver cyanide, silver thio cyanate and mixtures of two or more of the above-mentioned compounds.

The activated high purity alumina usable as a carrier material in the composite catalyst for the method of the present invention preferably contains 95% by weight or more, more preferably, 97% by weight or more, of pure alumina. Such type of activated alumina is prepared by heat-treating high purity alumina gel at a high temperature, preferably, of 400° to 600°C.

In order to disproportionation the hydrocabon mixture at a high disproportionation conversion, it is preferable that the activated high purity alumina contains no or a very small amount of alkali metal and silica. Particularly, it is preferable that the content of the alkali metal compounds is 0.5% by weight or less, more preferably 0.1% by weight or less, and the content of the silica is 5% by weight or less, more preferably, 3% by weight or less. This will become apparent by reading Comparison Example 4 illustrated hereinafter. The activated high purity alumina may be in any form of powder, grain, particle, lump and tablet. However, in order to easily prepare the composite catalyst, it is preferable that the activated high purity alumina is in the form of grains having a diameter of 2 to 10 mm or of fine particles having a 10 to 50 mesh size.

The activated high purity alumina may be used as the carrier material without preliminary heat-treatment or after the preliminary heat treatment at a temperature of 500° to 800°C for 1 to 5 hours in an inert atmosphere, for example, nitrogen gas or air atmosphere.

If the barium or strontium compound deposited in an amount more than 5 parts by weight onto 100 parts by weight of the activated high purity alumina carrier, the disproportionation conversion of the hydrocarbon mixture is undesirably low. If the amount of the barium or strontium compound deposited onto the carrier is less than 0.5 parts by weight, the content of $C_{+6}$ in the disproportional product undesirably increases. If the silver compound is deposited in an amount more than 20 parts by weight or less than 1 part by weight, the disproportionation conversion of the hydrocarbon mixture is undesirably low.

The barium or strontium compound and the silver compound as specified above may be deposited onto the activated alumina carrier by conventional methods, for example, the impregnation method wherein the activated alumina carrier is impregnated with a solution of both the compounds and then, dried to prepare the precursory catalyst. The precursory composite catalyst may be calcined at a temperature of 300° to 900°C, preferably, 500° to 600°C, for 1 to 5 hours. The calcination is may be carried out in a nitrogen gas or an air atmosphere, by a conventional calcination method, for example, using an electric furnace.

The hydrocarbon mixture usable for the method of the present invention contains isobutene and n-butene.

It is prefeable that isobutene in the hydrocarbon mixture be in an amount of 30% or more, more preferably, 30 to 60% by weight. In the conventional disproportionation method for butenes, it is known that an increase in the butene-1 content in the hydrocarbon mixture causes an undesirable increase in the content of n-pentenes in the $C_5$ fraction. However, in the disproportionation step of the method of the present invention, butene-1 in the hydrocarbon mixture is isomerized to butene-2 and simultaneously disproportionated. That is, in the method of the present invention the n-butene may contain butene-1. Accordingly, in the method of the present invention, the undesirable production of n-pentene is very little. That is, the $C_5$ fraction produced by the process of the present invention includes a very high content of isopentene; in other words, it consists essentially of isopentene.

The hydrocarbon mixture usable for the method of the present invention may contain, other than isobutene and n-butene, hydrocarbons such as n-butane, isobutane, propylene, propane, 1,3-butadiene, isopentane, isopentene, isoprene, n-pentane, pentene-1 and pentene-2. It is preferable that the total content of the other hydrocarbons contained in the hydrocarbon mixture be not higher than 15% by weight. Especially, it is desirable for the content of conjugated diene compounds, for example, 1,3-butadiene and isoprene, to be in a very small amount, 1.0% by weight or less.

The hydrocarbon mixture usable for the method of the present invention may be a so-called spent BB fraction which is an extraction residue prepared by extracting 1,3-butaniene from a fraction of distillate consisting of hydrocarbons having 4 carbon atoms ($C_4$ fraction) produced by thermal decomposition or catalytic cracking of natural gas, petroleum gas, naphtha or other petroleum fraction.

In the disproportionation step in the method of the present invention, there is no limitation in feed rate of the hydrocarbon mixture. However, it is preferable that the hydrocarbon mixture be brought into contact with the catalyst at a flow rate, per 1 cm³ of the catalyst, of 50 to 1,200 Ncm³/hour, more preferably, 100 to 700 Ncm³/hour calculated in terms of volume under the standard conditions of a temperature of 0°C and a pressure of 760 mmHg. In the method of the present invention, the smaller the flow rate of the hydrocarbon mixture, the higher the disproportionation conversion and the content of $C_5$ fraction in the disproportionation product, and the larger the flow rate of the hydrocarbon mixture, the lower the disproportionation conversion.

In the method of the present invention, the disproportionation operation is carried out at a temperature of 200° to 350°C. The disproportionation at a temperature lower than 200°C results in an undesirably low disproportionation conversion and an undesirably very high content of the $C_{+6}$ fraction in the disproportionation product. Also, the disproportionation at a temperature higher than 350°C causes an undesirable increase in the contents of the $C_{+6}$ fraction and decomposition products, for example, ethylene in the disproportionation product and a decrease in content of isopentene.

Accordingly, the temperature less than 200°C or more than 350°C are unsuitable for the practical disproportionation process in the method of the present invention.

Disproportionation in the method of the present invention is preferably carried out under normal pressure or a pressurized condition up to 10 kg/cm²G.

When the hydrocarbon mixture containing isobutene and n-butene is disproportionated by the method of the present invention, the resultant disproportionation product consists essentially of propylene, hydrocarbons having five carbon atoms ($C_5$ fraction) and hydrocarbons having 6 or more carbon atoms ($C_{+6}$ fraction). Both the $C_5$ fraction and $C_{+6}$ fraction consist of olefins. The content of the $C_{+6}$ fraction in the disproportionation product does not exceed 25% by weight. The $C_5$ fraction contains an isopentene content of not less than 95%. Accordingly, the method of the present invention produces high yields of propylene and isopentene which are very useful to the chemical industry. Further, isopentene obtained by the method of the present invention can be readily isolated and purified by conventional methods. That is, the $C_5$ fraction can be isolated from the reaction mixture by distillation at a temperature of 20° to 40°C under normal pressure. The $C_5$ fraction thus isolated consists essentially of isopentene and, therefore, can be subjected to an isoprene producing process wherein the isopentene is dehydrogenated.

The present invention will be further illustrated by the following examples which are given for purposes of illustration only and not as limitations to the scope of the present invention.

In the following examples and comparison examples, composition of the disproportionation product was determined by the method detailed below. After the disproportionation process was completed, the reaction mixture was subjected to gas chromatography analysis to determine and record amounts of the component hydrocarbons in the reaction mixture. From the record of the gas chromatographic analysis which contains the analysis results of all the component compounds in the reaction mixture, the analysis results of the disproportionation product hydrocarbons were isolated from the analysis results of the non-reacted hydrocarbons in the reaction mixture. From said isolated analysis results, the contents of the component hydrocarbons in the disproportionation product were calculated in %, based on the weight of the disproportional product. Also, the contents of the $C_5$ fraction and the $C_{+6}$ fraction were calculated from the result of the gas chromatography analysis in the same manner as stated above. Further, the content of isopentene was calculated on the basis of the weight of the $C_5$ fraction. The disproportionation conversion ratio was calculated as a ratio in percent of the weight of the disproportionation product to the original weight of the hydrocarbon mixture subjected to the disproportionation process.

EXAMPLES 1 THROUGH 3

In Example 1, in order to prepare a composite catalyst, an active high purity alumina (trademark: Neobeat, made by Mizusawa Chemical Industries Co., Ltd., Japan) containing 97% weight or more of alumina ($Al_2O_3$), 0.2% by weight of silica ($SiO_2$) and 0.01% by weight of sodium oxide ($Na_2O$) was reduced to fine particles having a 14 to 32 mesh size. After the activated alumina was heat-treated at a temperature of 550°C for 3 hours in a dried air atmosphere, the heat-treated activated alumina was impregnated with an aqueous solution of 2.3% by weight of silver nitrate and 0.6% by weight of barium nitrate, dried at a temperature of 100° to 120°C for 24 hours and calcined at a temperature of 600°C for 4 hours in an air atmosphere. The resultant composite catalyst contained the silver component and the barium component in the amounts indicated in Table 1 per 100 parts by weight of the activated alumina. The silver component amount was calculated in terms of silver metal and the barium component amount was in terms of barium oxide.

A spent BB fraction gas consisting essentially of 46.3% by weight of isobutene, 14.7% by weight of butene-2, 27.0% of weight of butene-1, 1.2% by weight of isobutene, 10.7% by weight of n-butane, 0.1% by weight of the sum of propane, propylene, 1.3-butadiene and propadiene, was fed into a reactor at a flow rate of 500 Ncm³/cm³.catalyst/hr and brought into contact with 6 cm³ of the above-prepared composite catalyst located within the reactor at a temperature of 250°C under normal pressure to effect the disproportionation of the spent BB fraction.

In Examples 2 and 3, operations identical to those in Example 1 were repeated, except that the concentrations of the silver nitrate and barium nitrate in the aqueous solutions were respectively 2.3% by weight and 1.2% by weight (Example 2) and 2.3% by weight and 1.8% by weight (Example 3) and the silver component and the barium component on the activated alumina carrier were in the amounts indicated in Table 1.

Table 1 indicates the disproportionation conversion ratios in the above examples, contents of the resultant isopentene in $C_5$ fractions and compositions of the disproportionation products, at the stage 2.5 hours after the start of the disproportionation process in Examples 1 through 3.

Table 1

| Item Example No. | Amount of Silver Component (Part by Weight) | Amount of Barium Component (Part by Weight) | Disproportionation conversion (%) | Content of Isopentene in $C_5$ Fraction (%) | Composition of Disproportionation Product (%) | | |
|---|---|---|---|---|---|---|---|
| | | | | | Propylene | $C_5$ Fraction | $C_{+6}$ Fraction |
| 1 | 4.3 | 1.1 | 25.5 | 100 | 26.9 | 48.2 | 24.9 |
| 2 | 4.3 | 2.2 | 22.5 | 100 | 30.1 | 51.1 | 18.8 |
| 3 | 4.3 | 3.3 | 14.7 | 100 | 33.4 | 58.7 | 7.9 |

EXAMPLES 4 THROUGH 10

In each of the Examples 4 through 10, the same procedures as in Example 2 were carried out except that the concentration of the silver nitrate in aqueous solution and the amount of the silver component on the activated almina carrier were as indicated in Table 2.

The results 2.5 hours after the start of the disproportionation process are indicated in Table 2.

Table 2

| Item<br>Example No. | Concentration of Silver Nitrate (%) | Amount of Silver Component (Part by Weight) | Disproportionation conversion (%) | Content of Isopentene in $C_5$ Fraction (%) | Composition of Disproportionation Product (%) | | |
|---|---|---|---|---|---|---|---|
| | | | | | Propylene | $C_5$ Fraction | $C_{+6}$ Fraction |
| 4 | 0.5 | 1 | 17.1 | 100 | 30.9 | 54.0 | 15.1 |
| 5 | 1.1 | 2 | 20.5 | 100 | 30.0 | 53.2 | 16.8 |
| 6 | 1.6 | 3 | 19.1 | 100 | 28.7 | 51.0 | 20.3 |
| 7 | 2.6 | 5 | 21.0 | 100 | 29.9 | 51.4 | 18.7 |
| 8 | 3.7 | 7 | 22.7 | 100 | 30.0 | 51.1 | 18.9 |
| 9 | 5.2 | 10 | 21.3 | 100 | 29.4 | 51.1 | 19.5 |
| 10 | 7.9 | 15 | 17.6 | 100 | 31.7 | 53.8 | 14.5 |

EXAMPLES 11 THROUGH 14

In each of the Examples 11 through 14, procedures indentical to those in Example 7 were effected, except that the hydrocarbon mixture was fed into the reactor at the flow rate indicated in Table 3. The results 2.5 hours after the start of the disproportionation process are indicated in Table 3.

Table 3

| Item<br>Example No. | Flow Rate of Hydrocarbone Mixture ($Nem^3$/$cm^3$ Catalyst/Hr) | Disproportionation Conversion (%) | Content of Isopentene in $C_5$ Fraction (%) | Composition of Disproportionation Product (%) | | |
|---|---|---|---|---|---|---|
| | | | | Propylene | $C_5$ Fraction | $C_{+6}$ Fraction |
| 11 | 150 | 40.0 | 100 | 28.1 | 48.9 | 23.0 |
| 12 | 300 | 31.3 | 100 | 30.3 | 49.7 | 20.0 |
| 13 | 750 | 18.5 | 100 | 31.1 | 51.8 | 17.1 |
| 14 | 1000 | 14.7 | 100 | 32.4 | 50.7 | 16.9 |

EXAMPLE 15

In Example 15 operations identical to those in Example 7 were repeated, except that the disproportionation temperature was 300° in place of 250°C. At the stage 2.5 hours after the beginning of the disproportionation process, the contents of propylene, the $C_5$ fraction and $C_{+6}$ fraction in the disproportionation product were respectively 32.0, 50.8 and 17.2% by weight, the content of isopentene in the $C_5$ fraction was 99.0% and the disproportionation conversion was 17.9%.

EXAMPLE 16

In Example 16 procedures identical to those in Example 7 were carried out, except that the activated high purity alumina was of the trademark γ - Alumina made by Nikki Chemical Co., Ltd., Japan and consisted essentially of 97% by weight or more of pure alumina, 0.2% by weight of silica and 0.02% by weight of sodium oxide. At the stage 2.5 hours after the beginning of the disproportionation process, the contents of propylene, the $C_5$ fraction and $C_{+6}$ fraction in the disproportionation product were respectively 30.7, 51.6 and 17.7% by weight, the content of isopentene in the $C_5$ fraction 100% and the disproportionation conversion 22.8%.

EXAMPLES 17 THROUGH 19

In each of the Examples 17 through 19, the same procedures as in Example 7 were carried out, except that strontium nirate was used in an amount indicated in Table 4, and calculated in terms of strontium oxide, as a component of the composite catalyst in place of the barium nitrate. The results at the stage 2.5 hours after the start of the disproportionation process are indicated in Table 4.

Table 4

| Item<br>Example No. | Amount of Strontium Component (Part by Weight) | Disproportionation Conversion (%) | Content of Isopentene in $C_5$ Fraction (%) | Composition of Disproportionation Product (%) | | |
|---|---|---|---|---|---|---|
| | | | | Propylene | $C_5$ Fraction | $C_{+6}$ Fraction |
| 17 | 1.2 | 23.8 | 100 | 26.6 | 50.4 | 23.0 |
| 18 | 2.4 | 16.5 | 100 | 25.0 | 55.3 | 19.7 |
| 19 | 3.6 | 11.6 | 100 | 27.4 | 59.0 | 13.6 |

EXAMPLE 20

In Example 20 the same procedures as in Example 7 were repeated using barium chloride in place of barium nitrate. At the stage 2.5 hours after the start of the disproportionation process, the contents of propylene, the $C_5$ fraction and the $C_{+6}$ fraction in the disproportionation were respectively 32.8, 55.7, 11.5% by weight, the content of isopentene in the $C_5$ fraction was 100% and the disproportionation convertion was 18.3%.

EXAMPLE 21

In Example 21 the same operations as in Example 7 were repeated using silver carbonate in place of silver nitrate. At the stage 2.5 hours after the start of the disproportionation process, the contents of propylene, the $C_5$ fraction and the $C_{+6}$ fraction in the disproportionation product were respectively 29.4, 51.6 and 19.0% by weight, the content in the $C_5$ fraction was 100% and the disproportionation conversion was 19.8%.

COMPARISON EXAMPLES 1 THROUGH 3

In Comparison Examples 1 and 2, the same procedures as in Example 2 were carried out using no silver nitrate in Comparison Example 1 and no barium nitrate in Comparison Example 2.

In comparison Examples 3, operations identical to those in Example 7 were carried out, except that the disproportionation temperature was 400° in place of 250°C. The results at the stage 2.5 hours after the start of each disproportionationn process are indicated in Table 5.

Table 5

| Item | Disproportionation Temperature (°C) | Amount of Silver Component (Part by Weight) | Amount of Barium Component (Part by Weight) | Disproportionation Conversion (%) | Content of Isopentene in $C_5$ Fraction (%) | Composition of Disproportionation Product (%) | | |
|---|---|---|---|---|---|---|---|---|
| Example No. | | | | | | Propylene | $C_5$ Fraction | $C_{+6}$ Fraction |
| 1 | 250 | 0 | 2.2 | 13.7 | 100 | 23.1 | 49.5 | 27.4 |
| 2 | 250 | 4.3 | 0 | 22.9 | 100 | 17.0 | 35.0 | 48.0 |
| 3 | 400 | 5 | 2.2 | 6.4 | 92.0 | 15.9 | 41.8 | 40.0 |

Note:
The disproportionation product in Comparison Example 3 further contained 2.3% by weight of ethylene.

COMPARISON EXAMPLE 4

The same activated high purity alumina as used in Example 1 was reduced to fine particles having 14 to 32 mesh size and preliminarily heat-treated at a temperature of 800°C for 3 hours in an air atmosphere. The activated alumina thus heat-treated was impregnated with an aqueous solution containing 2.6% by weight of silver nitrate, 1.2% by weight of barium nitrate and 0.6% by weight of sodium hydroxide, dried at a temperature of 100° to 120°C for 24 hours and heat-treated at a temperature of 600°C for 4 hours in air flow. The resultant composite catalyst consisted of 100 parts by weight of the activated alumina, 5 parts by weight of the silver component calculated in terms of silver metal, 2.2 parts by weight of the barium component in terms of barium oxide and 1.3 parts by weight sodium conponent in terms of sodium oxide.

The same disproportionation operations as those in Example 1 were repeated. At the stage 2.5 hours after the start of the disproportionation process, the contents of propylene, the $C_5$ fraction and $C_{+6}$ fraction in the disproportionation product were respectively 11.7, 21.9 and 66.4% by weight, the content of isopentene in the $C_5$ fraction was 100% and the disproportionation conversion was 10.4%.

What we claim is:

1. A method for producing isopentene comprising the steps of:
   providing a composite catalyst which has been prepared from 100 parts by weight of a carrier material consisting of an activated high purity alumina, 0.5 to 5 parts by weight of a barium or strontium compound calculated in terms of an oxide thereof and 1 to 20 parts by weight of a silver compound calculated in terms of silver metal by depositing said barium or strontium compound and said silver compound onto said alumina carrier to produce a precursory composite catalyst and calcining the precursory composite catalyst at a temperature of 300° to 900°C,
   bringing a hydrocarbon mixture containing isobutene and n-butene into contact with said composite catalyst at a temperature of 200° to 350°C, and;
   isolating the resultant isopentene from the reaction mixture.

2. A method as claimed in claim 1, wherein said barium compound is selected from the group consisting of barium salts of inorganic acids, barium salts of organic acids having 1 to 6 carbon atoms, barium hydroxide, barium oxide, and mixtures of two or more of the above mentioned compounds.

3. A method as claimed in claim 2, wherein said barium salt of inorganic acid is selected from barium nitrate, barium sulfate, barium carbonate, barium chloride and mixtures of two or more of the above-mentioned compounds.

4. A method as claimed in claim 2, wherein said barium salts of organic acid is selected from the group consisting of barium formate, barium acetate, barium propionate, barium n-butyrate, barium isobutyrate, barium n-valerate, barium isovalerate, barium n-caproate, barium pivalate, barium acrylate, barium methacrylate, barium crotonate, barium oxalate, barium malonate, barium succinate and mixtures of two or more of the above-mentioned compounds.

5. A method as claimed in claim 1, wherein said strontium compound is selected from the group consisting of strontium salts of inorganic acids, strontium salts of organic acids having 1 to 6 carbon atoms, strontium oxide, strontium hydroxide and mixtures of two or more of the above-mentioned compounds.

6. A method as claimed in claim 5, wherein said strontium salt of inorganic acid is selected from the group consisting of strontium nitrate, strontium sulfate, strontium carbonate, strontium chloride and mixtures of two or more of the above-mentioned compounds.

7. A method as claimed in claim 5, wherein said strontium salt of organic salt is selected from the group consisting of strontium formate, strontium acetate, strontium propionate, strontium n-butyrate, strontium isobutyrate, strontium n-valerate, strontium isovalerate, strontium n-caproate, strontium pivalate, strontium acrylate, strontium methacrylate, strontium crotonate, strontium oxalate, strontium malonate, strontium succinate and mixtures of two or more of the above-mentioned compounds.

8. A method as claimed in claim 1, wherein said silver compound is selected from the group consisting of silver nitrate, silver sulfate, silver carbonate, silver halides, silver cyanide, silver thiocyanate and mixtures of two or more of the above-mentioned compounds.

9. A method as claimed in claim 1, wherein said alumina carrier contains at least 95% by weight of pure alumina.

10. A method as claimed in claim 1, wherein said alumina carrier is prepared by heat-treating alumina gel.

11. A method as claimed in claim 10, wherein said heat-treatment is carried out at a temperature of 400° to 600°C.

12. A method as claimed in claim 1, wherein said alumina carrier contains alkali metal compound in an amount of 0.5% by weight or less, and silica in an amount of 5% by weight or less.

13. A method as claimed in claim 1, wherein said alumina carrier is in the form of grain having a diameter of 2 to 10 mm.

14. A method as claimed in claim 1, wherein said alumina carrier is in the form of fine particles having a 10 to 50 mesh size.

15. A method as claimed in claim 1, wherein said alumina carrier is preliminarily heat-treated in an inert gas atmosphere at a temperature of 500° to 800°C.

16. A method as claimed in claim 1, wherein said hydrocarbon mixture contains 30% by weight or more of isobutene.

17. A method as claimed in claim 16, wherein said content of isobutene is 30 to 60% by weight.

18. A method as claimed in claim 1, wherein said hydrocarbon mixture is brought into contact with said catalyst is a flow rate of 50 to 1,200 $Ncm^3/hr$ per 1 $cm^3$ of said composite catalyst.

19. A method as claimed in claim 18, wherein said flow rate of said hydrocarbon mixture is 100 to 700 $Ncm^3/hr$ per 1 $cm^3$ of said composite catalyst.

20. A method as claimed in claim 1, wherein said isolating of said resultant isopentene is carried out by distillation at a temperature of 20° to 40°C under normal pressure.

21. A method as claimed in claim 1, wherein said contact of said hydrocarbon mixture with said composite catalyst is carried out under normal pressure or under a pressurized condition up to 10 $kg/cm^2$ G.

* * * * *